United States Patent
Hansen

(12) 
(10) Patent No.: US 9,241,997 B2
(45) Date of Patent: Jan. 26, 2016

(54) TREATMENT OF SYMPTOMS ASSOCIATED WITH BACTERIAL VAGINOSIS

(75) Inventor: Inge Dorthe Hansen, Vejle (DK)

(73) Assignee: IDH Holding ApS, Vejla (DK)

( * ) Notice: Subject to any disclaimer, the term of this patent is extended or adjusted under 35 U.S.C. 154(b) by 1351 days.

(21) Appl. No.: 10/560,519

(22) PCT Filed: Jun. 11, 2004

(86) PCT No.: PCT/DK2004/000410
§ 371 (c)(1),
(2), (4) Date: Mar. 20, 2006

(87) PCT Pub. No.: WO2004/110461
PCT Pub. Date: Dec. 23, 2004

(65) Prior Publication Data
US 2006/0154874 A1     Jul. 13, 2006

(30) Foreign Application Priority Data

Jun. 13, 2003   (DK) .................................. 2003 00885

(51) Int. Cl.
| | | |
|---|---|---|
| A61K 31/7016 | (2006.01) | |
| A61K 31/70 | (2006.01) | |
| C13K 5/00 | (2006.01) | |
| A61K 45/06 | (2006.01) | |

(52) U.S. Cl.
CPC ................ *A61K 45/06* (2013.01); *A61K 31/70* (2013.01); *A61K 31/7016* (2013.01)

(58) Field of Classification Search
CPC ... A61K 31/70; A61K 31/7016; A61K 45/06; A61K 2300/00
USPC .......................... 514/23, 53, 54, 24, 398, 967; 536/123.13, 123.1
See application file for complete search history.

(56) References Cited

U.S. PATENT DOCUMENTS

| | | | | |
|---|---|---|---|---|
| 2,895,993 | A * | 7/1959 | Stephens, Jr. .................. | 552/203 |
| 3,070,498 | A * | 12/1962 | Prince et al. .............. | 514/254.02 |
| 3,860,707 | A * | 1/1975 | Wootton .......................... | 514/53 |
| 5,084,277 | A * | 1/1992 | Greco et al. .................. | 424/433 |
| 5,314,904 | A * | 5/1994 | Egidio et al. .................. | 514/394 |
| 6,440,949 | B1 * | 8/2002 | Zeng ............................. | 514/58 |
| 2002/0035119 | A1 | 3/2002 | Kumar et al. | |
| 2003/0017207 | A1 * | 1/2003 | Lin et al. ........................ | 424/486 |

FOREIGN PATENT DOCUMENTS

| | | | |
|---|---|---|---|
| DE | 1959402 A | * | 6/1971 |
| GB | 681105 | | 10/1952 |
| WO | WO-99/63970 | | 12/1999 |
| WO | WO-00/35460 | | 6/2000 |

OTHER PUBLICATIONS

Ozmen et al.(Turkish Journal of Medical Sciences (1998), 28 (2), pp. 171-173) (Abstract Sent).*
STN Abstract of Woitun et al., DE 1959402 A, Jun. 3, 1971 (Abstract sent).*
Schwebke et al., Sexually Transmitted Diseases: vol. 29(1) Jan. 2002, pp. 59-64.*
Ozmen et al. (Turkish journal of Medical Sciences (1998), 28 (2), pp. 171-173).*
Woitun et al.; DE 1959402 A, Jun. 3, 1971 (English Translation by Machine).*
Aroutcheva et al, Defense factors of vaginal lactobacilli, Department of Obstretrics and Gynecology, Rush-Presbyterian, St. Luke's Medical Center, Chicago, Illinois, Sep. 6, 2000.
Olsen, Eva, Vaginal infections after a course of antibiotics, Helse Nr. 2, 2000.
Ohara, Y. et al., Tablet for treating hyperlipidemia, comprises compression-molded formulation comprising mixture of pravastatin sodium and additive which comprises synthetic calcium silicate as a stabilizer, WPI Abstract No. 2001-613851 for JP2001233766, Aug. 28, 2001.
Yoshimura, T., Preparation of high calcium content medicine, medical drinks, etc. containing active substance powder or extract of chrysanthemum, WPI Abstract No. 1988-215499 for JP63150227, Jun. 22, 1988.
Adriaens, E. et al., Mucosal Irritation Potential of Personal Lubricants Relates to Product Osmolality as Detected by the Slug Mucosal Irritation Assay, *Sexually Transmitted Diseases*, 35(5): 512-16, May 2008.
Zeng, Z. et al., Directed shift of vaginal flora after topical application of sucrose gel in a phase III clinical trial: a novel treatment for bacterial vaginosis, *Chinese Medical Journal*, 123(15): 2051-57, 2010.

* cited by examiner

*Primary Examiner* — Shaojia Anna Jiang
*Assistant Examiner* — Michael C Henry
(74) *Attorney, Agent, or Firm* — Dinsmore & Shohl LLP

(57) ABSTRACT

The invention relates to the use of saccharide, such as lactose for the preparation of a medicament for the treatment and/or prophylaxis of one or more symptoms caused by bacterial vaginosis, wherein the medicament comprises at least 20 percent by weight of saccharide, and wherein the medicament is substantially free from bacteria. Furthermore, the invention relates to a method for treating one or more symptoms associated with bacterial vaginosis, as well as a pharmaceutical composition comprising the saccharide.

15 Claims, No Drawings

TREATMENT OF SYMPTOMS ASSOCIATED WITH BACTERIAL VAGINOSIS

All patent and non-patent references cited in the present application are hereby incorporated by reference in their entirety.

FIELD OF INVENTION

The present invention relates to a high saccharide concentration medicament and the uses thereof for the treatment, amelioration and/or prophylaxis of symptoms associated with bacterial vaginosis.

BACKGROUND OF INVENTION

Bacterial Vaginosis (BV) is a clinical syndrome characterised by malodorous discharge. Bacterial Vaginosis is the most common type of vaginal infection in women of reproductive age, accounting for 45% of all vulvovaginal infections. Moreover, it has been related to a variety of upper genital tract infections and obstetrical complications. These include pelvic inflammatory disease (PID), post-Caesarean endometritis, posthysterectomy pelvic infection, chorioamnionitis, premature rupture of membranes (PROM) and preterm labour and delivery. The prevention of these infections for a woman and her child is an important issue in women's health (1).

Fifteen percent of gynaecologic patients and 10-30 percent of pregnant women have BV, whilst up to 60 percent of women visiting a clinic for sexually transmitted diseases are estimated to suffer from BV (1).

Bacterial Vaginosis has been associated with non-white race, sexual activity and the intra-uterine device, but no precise studies are available. There are indications of sexual transmission of the disease, but other routes are also indicated.

The normal vaginal flora is dominated by lactobacilli which account for 95 percent of the bacteria present in the vagina, with other facultative and anaerobic bacteria present in only small numbers. Bacterial Vaginosis represents a complex change in the vaginal ecosystem characterised by a reduction in the prevalence and concentration of lactobacilli and an increase in the prevalence and concentration of *Gardnerella vaginalis*, anaerobic gram-negative rods, and *Mycoplasma hominis*. In BV, a flora consisting primarily of benign lactobacilli is replaced by a flora consisting of high concentrations of potentially virulent bacteria. Lactobacilli maintain the acid pH in the vagina by producing lactic acid which maintains a low pH of normally less than 4.5. Low pH directly inhibits the growth of anaerobic organisms. Hydrogen peroxide-producing lactobacilli also appear to play a role in limiting *Gardnerella* and the anaerobic flora of the vagina (1). Moreover the especially virulent *Prevotella* and *Porphyromonas* species are present in particular high numbers in patients with BV (1).

When affected women are symptomatic, they complain predominantly of vaginal odour. The odour is described as fishy. Patients often refer to embarrassing vaginal odour especially after intercourse. About 90 percent of patients also notice a mild to moderate discharge. Pain symptoms are rare because the infection is not linked to inflammation of the tissue. Patients with BV may not display the symptoms that would normally alert their physicians to the infection. In fact, nearly half of the patients with BV do not complain of excess or malodorous vaginal discharge.

The diagnosis requires three of the following signs to be present:

1. A homogenous, white or grey, noninflammatory discharge that adheres to the vaginal wall.
2. The presence of clue cells (>20% of the epithelial cells in 400× magnification) on microscopic examination of fresh smears.
3. The pH of vaginal secretions greater than or equals 4.7.
4. A fishy odour of vaginal discharge before or after adding of 10% KOH.

Culture of *Gardnerella vaginalis* is not recommended as a diagnostic tool, as it is not specific.

A study showed that patients with BV had a 5.1-fold higher risk of post-partum endometritis following Caesarean section than did patients with a lactobacilli-dominant flora.

Patients with BV have a four times higher rate of vaginal-cuff cellulitis following abdominal hysterectomy than patients with a lactobacillus-dominant flora (1).

The rate of post-abortion pelvic inflammatory disease was three times less in patients treated with a BV-effective antibiotic related to placebo-treated patients. Prematurity occurs 1.9 times more commonly, and premature rupture of membranes occurs 3.5 times more commonly in women with BV than in those without BV. BV bacteria are frequently isolated from amniotic fluid and could play a major role in premature delivery (1).

The established medicine offers the treatment of either of two antibiotics, clindamycin or metronidazole, either topically or by the oral route.

Metronidazole as a 7-day treatment has an 80-90% cure rate after 1 month. Side effects are nausea, abdominal cramps and a metallic taste. The patient must refrain from alcohol intake, as it may produce antabuse effects. It is not recommended in the first trimester of pregnancy.

Clindamycin as a 7-day treatment has equal effects as metronidazole, and its side effects are less, though diarrhoea is possible. Concerns about Clostridium difficile colitis have prevented the widespread use.

Topical application through vaginal preparations has minimised side effects; however, this approach is more expensive.

The cure rate is high but a significant proportion of women suffer relapses and recurrences. There is some evidence that residual biochemical and microbiological abnormalities persist in these women (2).

Different alternative measures have been advised (live yoghurt bacteria, *Lactobacillus acidophilus* preparations, acetic acid flushes (several hits on the Internet). Studies of live yoghurt or *Lactobacillus acidophilus* have not demonstrated benefits (3).

In U.S. Pat. No. 6,440,949 a method for increasing the acidity in vagina is suggested. The method suggests to administer an amount of 2.5% to 17% (w/v) of one or more saccharides in an acidic medicament. The patent tests different concentrations of saccharides, but none of the concentrations shows a significant decrease in pH, and furthermore, none of the concentrations shows elimination of the odour causing bacteria, the Gram negative bacteria (G-b). In U.S. Pat. No. 6,440,949, no relation is shown between the concentration of the saccharide and the results obtained.

SUMMARY OF INVENTION

The present invention relates to the treatment of one or more of the symptoms associated with bacterial vaginosis, in particular treatment or amelioration of the odour normally associated with bacterial vaginosis.

Accordingly, in one aspect the invention relates to the use of saccharide, said saccharide being fermented by lactic acid bacteria, for the preparation of a medicament for the treatment, amelioration and/or prophylaxis of one or more symptoms caused by bacterial vaginosis, wherein the medicament comprises at least 20 percent by weight of saccharide, and wherein the medicament is substantially free from bacteria.

Furthermore, the fermentation by the lactic acid bacteria in vagina leads to a high concentration of acid whereby the malign bacteria are inhibited and the symptom-free period after treatment is prolonged. If needed, the treatment can be prolonged without limitations as no adverse side effects occur.

In another aspect the invention relates to a method for the treatment, amelioration and/or prophylaxis of one or more symptoms associated with bacterial vaginosis in an individual, comprising administering an effective amount of a medicament comprising a saccharide to said individual, said saccharide being fermented by lactic acid bacteria, wherein the medicament comprises at least 20 percent by weight of said saccharide, and wherein the medicament is substantially free from bacteria.

In yet another aspect the invention relates to a pharmaceutical composition for vaginal application, comprising a saccharide, wherein the saccharide constitutes at least 20 percent by weight of the pharmaceutical composition, and wherein the composition is substantially free from bacteria.

In a further aspect the present invention relates to a kit-of-parts comprising the pharmaceutical composition as defined above and an anti-fungal agent and/or an antibacterial agent for simultaneous, sequential or separate use.

In another aspect the invention relates to a kit-of-parts comprising the pharmaceutical composition as defined above and at least one pH measurement means, for measuring vaginal pH.

DETAILED DESCRIPTION OF THE INVENTION

As described above, the present invention relates in one aspect to the use of saccharide, said saccharide being fermented by lactic acid bacteria, for the preparation of a medicament for the treatment and/or prophylaxis of one or more symptoms caused by bacterial vaginosis, wherein the medicament comprises at least 20 percent by weight of saccharide, and wherein the medicament is substantially free from bacteria.

The symptoms associated with bacterial vaginosis may be:
A homogenous, white or grey, noninflammatory discharge that adheres to the vaginal wall
A fishy odour from vagina
Pruritus of vulva
Pain By the term "symptoms associated with bacterial vaginosis" is meant that the medicament may be used for treating the symptoms, independent of whether the diagnosis of bacterial vaginosis has been established according to the criteria set forth above.

The present invention may be used for treating, ameliorating and/or preventing any one of the above symptoms, and in particular the symptom treated, ameliorated and/or prevented with the present invention is the fishy odour.

The present inventor has found that a high concentration of saccharides alleviates the symptoms associated with bacterial vaginosis and prolongs the period without symptoms after treatment. The medicament comprises at least 20 percent by weight of saccharide; it is, however, preferred that the saccharide medicament comprises even more saccharide. In a preferred embodiment the medicament is a saccharide suspension or pure saccharide, such as a saturated saccharide suspension, such as dry powder in tablets or capsules.

Accordingly, the medicament preferably comprises at least 25 percent by weight of the saccharide, such as at least 40 percent by weight of saccharide, such as at least 50 percent by weight of saccharide, such as at least 75 percent by weight of saccharide, such as at least 90 percent by weight of saccharide, such as at least 95 percent by weight of saccharide, such as at least 98 percent by weight of saccharide, such as 100 percent by weight of saccharide. The term "percent by weight" is used in its normal meaning, i.e. grammes (g) of saccharide in grammes of the medicament.

It is of importance that the medicament is substantially free from bacteria, in particular substantially free from lactic acid bacteria. By the term "substantially free from bacteria" is meant that the medicament includes less than $10^5$ bacteria per dosage, such as less than $10^4$ bacteria per dosage, such as less than $10^3$ bacteria per dosage, such as less than $10^2$ bacteria per dosage. In particular the medicament includes less than $10^5$ lactic acid bacteria per dosage, such as less than $10^4$ lactic acid bacteria per dosage, such as less than lactic acid $10^3$ bacteria per dosage, such as less than $10^2$ lactic acid bacteria per dosage. Lactic acid bacteria are for example *Lactobacillus acidophilus, Streptococcus thermophilus, Bifidobacterium longum*.

Furthermore, it is preferred that the medicament according to the invention also treats or prevents the bacterial vaginosis. This may be examined by measuring the vaginal pH. A vaginal pH is normally less than 4.5. Accordingly, a decrease in vaginal pH to below 4.7, more preferably below 4.5, is an indication that the bacterial vaginosis has been treated.

The saccharide according to the invention is any suitable saccharide, wherein the saccharide is fermented by lactic acid bacteria. Preferably the saccharide is not fermented by *Gardnerella vaginalis*.

Accordingly, in a preferred embodiment the saccharide is selected from a disaccharide and a monosaccharide, such as a saccharide selected from lactose and saccharose, preferably selected from lactose. When using lactose, it is preferred that the lactose is in its original disaccharide form, and not degraded.

The medicament may comprise one type of saccharide or a mixture of saccharides, wherein all saccharides are suitable according to the invention.

The medicament according to the invention is useful for treating, ameliorating, and/or preventing symptoms associated with bacterial vaginosis as defined above independent of the bacteria causing the vaginosis. In particular the medicament is used for treating, ameliorating and/or preventing symptoms caused by bacteria selected from *Gardnerella vaginalis*, Gram negative rods, and *Mycoplasma hominis*. More specifically the medicament is used for treating, ameliorating and/or preventing symptoms caused by bacteria selected from anaerobic Gram negative rods.

The medicament according to the invention is preferably applied directly into the vagina, and therefore, the medicament is preferably formulated for topical application. Accordingly, the medicament may have any suitable form for topical administration. In one embodiment the medicament is in the form of a vaginal suppository gel. In another embodiment the medicament is in the form of a vaginal capsule. In yet another embodiment the medicament is in the form of a vaginal tablet. In a further embodiment the medicament is in the form of a suspension.

The medicament preferably comprises a pharmaceutical composition comprising a saccharide as described herein optionally mixed with suitable pharmaceutically acceptable additives and/or carriers. The saccharide may be formulated in any suitable manner, for example in form of a monohydrate.

Examples of pharmaceutically acceptable additives and carriers are polyethylene glycols, glycerol, agar agar, carrageenan, modified starches, stearates, and water. In particular it is preferred that the additives or carriers are not based on protein, since a protein source may counteract the beneficial effects of the medicament. In a preferred embodiment the additive is magnesium stearate or sodium stearate.

In one aspect the invention further relates to a pharmaceutical composition comprising the saccharide as described above in the concentrations described above and optionally further comprising pharmaceutically acceptable additives and/or carriers.

The pH of the pharmaceutical composition before application to the vagina is preferably in the range of from 5.5 to 8.0, such as from 6.5 to 7.5, more preferably about 7.0.

The conservation of the product is preferably secured by low water activity, optionally aseptic production and packaging, and if needed, sorbic acid or paraben preservatives.

The medicament according to the invention has a long shelf life at ambient temperature.

In a further aspect the invention relates to a method of treating, ameliorating and/or preventing symptoms associated with bacterial vaginosis, wherein the method comprises administering an effective amount of a medicament comprising a saccharide, wherein the saccharide is as defined above.

The medicament may be administered one or more times per day, as necessary for a period of from 1 to 7 days, but if needed, the treatment can be prolonged without limitations.

Furthermore, the medicament may be administered intermittently according to the needs of the individual to be treated.

The medicament is preferably administered in dosages, wherein one dosage unit may be from 10 mg to 10 g of medicament. In a more preferred embodiment, the dosage unit is from 1-5 g of medicament.

The saccharides are the essential active component of the medicament according to the invention, and can fulfil the object of the invention. However, for some treatment regimens, it is preferred that the medicament further includes an effective amount of another medicament.

Accordingly, in one embodiment the medicament further includes an anti-fungal agent. Examples of anti-fungal agents are ketoconazole, terconazole, itraconazole, and fluconazole.

In another embodiment the medicament further includes an effective amount of an anti-bacterial agent. Examples of suitable anti-bacterial agents are metronidazole and clindamycin.

In another aspect the invention relates to a combination product or a kit-of-parts product comprising the pharmaceutical composition as defined above and an antifungal agent and/or an anti-bacterial agent for simultaneous, sequential or separate use. The anti-fungal and anti-bacterial agent is preferably as described above.

In order to test the functionality of the medicament, the medicament of the invention may also be commercialised as a kit-of-parts comprising the pharmaceutical composition as defined above and at least one pH measurement means, for measuring vaginal pH.

The pH measuring means is preferably a pH indicator strip, such as an indicator strip from Merck showing pH in the interval 4.0-7.0. The pH measuring means may be applied directly to the vaginal mucosa for measurement.

EXAMPLES

Example 1

Vaginal Suppository Gel
Ingredients:

| | |
|---|---|
| Lactose, spray-dried (alpha monohydrate) | 40% |
| Macrogol (polyethylene glycols) 1000 | 5% |
| Macrogol (polyethylene glycols) 3000 | 5% |
| Parabens* | 0.1% |
| Disodium hydrogen phosphate | 0.1% |
| Water | 49.8% |
| pH 7.0 | |

*8:2 mixture of methyl- and propyl pars hydroxy benzoate

The ingredients are mixed homogeneously, the resulting suspension is sterilised by means of heat and dispensed aseptically into sterile packaging.

1 dosage=1-3 ml

Example 2

| Vaginal suppository gel | |
|---|---|
| Lactose, spray-dried (alpha monohydrate) | 40% |
| Glycerol | 15% |
| Agar agar | 2% |
| Disodium hydrogen phosphate | 0.1% |
| Water | 42.9% |
| pH 7.0 | |

The ingredients are heated to boiling point and mixed homogeneously. They are then sterilised by heat and dispensed aseptically into sterile packaging.

1 dosage=1-3 ml

Example 3

| Vaginal suppository gel | |
|---|---|
| Lactose, spray-dried (alpha monohydrate) | 50% |
| Glycerol | 15% |
| Carrageenan (Iota or mixture) | 0.8% |
| Disodium hydrogen phosphate | 0.1% |
| $CaCl_2$ | 0.1% |
| Water | 34% |
| pH 7.0 | |

The ingredients are heated to boiling point and mixed homogeneously. They are then sterilised by heat and dispensed aseptically into sterile packaging.

1 dosage=1-3 ml

Example 4

Vaginal Capsule

Lactose, spray-dried (alpha monohydrate)

Encapsulated in capsules produced from modified starches

Capsules are prepared in a conventional manner.

Dosage: 0.5-3 grammes

Example 5

| Vaginal tablets | |
| --- | --- |
| Lactose, Fast Flo | 90% |
| Starch 1500 (modified starch) | 10% |

The ingredients are mixed homogeneously, and the resulting mixture is pressed into tablets in a conventional manner. Raw materials of good microbiological quality and hygienic production facilities secure the required microbiological quality.
Dosage: 0.5-3 grammes

Example 6

| Vaginal tablets | |
| --- | --- |
| Lactose, spray-dried (alpha monohydrate) | 95% |
| Polyethylene glycol | 5% |

The ingredients are mixed homogeneously, and the resulting mixture is pressed into tablets in a conventional manner. Raw materials of good microbiological quality and hygienic production facilities secure the required microbiological quality.
Dosage: 0.5-3 grammes

Example 7

| Vaginal tablets | |
| --- | --- |
| Lactose, spray-dried (alpha monohydrate) | 100% |

The lactose is pressed into tablets in a conventional manner. Raw materials of good microbiological quality and hygienic production facilities secure the required microbiological quality.
Dosage: 0.5-3 grammes

Example 8

| Suspension | |
| --- | --- |
| Lactose, spray-dried (alpha monohydrate) | 50% |
| Disodium hydrogen phosphate | 0.1% |
| Water | 49.9% |
| pH | 7.0 |

The ingredients are mixed homogeneously, and the resulting suspension is sterilised by means of heating.
1 dosage=1-3 ml by use of an application device

Example 9

Treatment

A female had suffered from discomfort and vaginal secretions of fishy smell recurring after two 7-day treatments with metronidazole. The vaginal pH was approximately 5.3, varying between 5.0 and 5.5.

A lactose suspension (1-3 ml) as prepared in Example 8 was instilled into the vagina twice daily. After approximately 24 hours the pH lowered to 4.7 and the fishy odour disappeared. Continuous application once a day further lowered the pH down to approximately 4.4. The treatment was continued for 4 days.

After 4 days symptoms such as the fishy odour recurred; however, the symptoms disappeared after one day of the treatment described above.

REFERENCES

1. SOGC Clinical Practice Guidelines No. 14 Mar. 1997. Bacterial vaginosis.
2. Priestley, Cecilia J F, and G R Kinghorn. "Bacterial Vaginosis." *British Journal of Clinical Practice* 50, No. 6 (September 1996): 331-334.
3. Larsson, P. G. Treatment of bacterial vaginosis. Int. J. STD AIDS 1992; 3: 239-247.
4. *Gardnerella vaginalis* (2003) M. J. Pickett, James R. Greenwood, Sydney M. Harvey.

The invention claimed is:

1. A method for the treatment and/or amelioration of one or more symptoms of bacterial vaginosis, comprising administering to an individual having one or more symptoms of bacterial vaginosis a pharmaceutical dosage unit of 10 mg to 10 g in the form of a vaginal capsule or tablet, said pharmaceutical dosage unit consisting essentially of at least 90% by weight of lactose monohydrate as the only active ingredient, and wherein said pharmaceutical dosage unit includes less than $10^5$ bacteria, thereby treating and/or ameliorating symptoms of bacterial vaginosis.

2. The method according to claim 1, wherein one symptom is unpleasant vaginal odour.

3. The method according to claim 1, wherein a symptom is pruritus of vulva.

4. The method according to claim 1, wherein the lactose monohydrate is substantially not fermented by *Gardnerella vaginalis*.

5. The method according to claim 1, wherein the bacterial vaginosis is caused by bacteria selected from *Gardnerella vaginalis*, Gram negative rods, and *Mycoplasma hominis*.

6. The method according to claim 5, wherein the bacterial vaginosis is caused by bacteria selected from anaerobic Gram negative rods.

7. The method according to claim 1, wherein the pharmaceutical dosage unit is formulated for topical application.

8. The method according to claim 1, wherein the pharmaceutical dosage unit is in the form of a vaginal capsule.

9. The method according to claim 1, wherein the pharmaceutical dosage unit is in the form of a vaginal tablet.

10. The method according to claim 1, wherein the pharmaceutical dosage unit is from 1-5 g.

11. The method according to claim 1, wherein the pharmaceutical dosage unit comprises one or more pharmaceutically acceptable additives and carriers selected from the group consisting of: polyethylene glycols, glycerol, agar agar, carrageenan, modified starches, stearates and water.

12. The method according to claim 11, wherein the pharmaceutically acceptable additive is magnesium stearate or sodium stearate.

13. A method for reducing vaginal pH to below 4.7, comprising administering to an individual having one or more symptoms of bacterial vaginosis an effective amount of a pharmaceutical dosage unit of 10 mg to 10 g in the form of a vaginal capsule or tablet for vaginal application said pharmaceutical dosage unit consisting essentially of:
   a) at least 90 percent by weight of lactose monohydrate as the only active ingredient and b) optionally one or more pharmaceutically acceptable additives, carriers and/or preservatives, wherein said dosage unit includes less than $10^5$ bacteria.

14. The method of claim 13 wherein the vaginal pH is reduced to below 4.5.

15. The method of claim 13 further comprising measuring said vaginal pH subsequent to said administering.

* * * * *